United States Patent [19]
Stopp et al.

[11] 4,139,558
[45] Feb. 13, 1979

[54] PROCESS FOR PREPARING FREE-FLOWING 2-NITRO-4-ACETYLAMINO-ANISOLE

[75] Inventors: Gerhard Stopp; Rolf Schimpf, both of Leverkusen, Fed. Rep. of Germany

[73] Assignee: Bayer Aktiengesellschaft, Leverkusen, Fed. Rep. of Germany

[21] Appl. No.: 774,093

[22] Filed: Mar. 3, 1977

Related U.S. Application Data

[63] Continuation of Ser. No. 613,832, Sep. 16, 1975, abandoned.

[30] Foreign Application Priority Data

Oct. 9, 1974 [DE] Fed. Rep. of Germany ....... 2448132

[51] Int. Cl.² ............................................ C07C 102/00
[52] U.S. Cl. ................................. 260/562 A; 260/688
[58] Field of Search ............................ 260/562 A, 688

[56] References Cited

U.S. PATENT DOCUMENTS

| | | | |
|---|---|---|---|
| 2,314,212 | 3/1943 | Hennion | 260/688 |
| 2,325,797 | 8/1943 | Pizzarello | 260/562 A |

*Primary Examiner*—Arthur P. Demers
*Attorney, Agent, or Firm*—Sprung, Felfe, Horn, Lynch & Kramer

[57] ABSTRACT

2-Nitro-4-acetylamino-anisole is prepared directly in the form of a moist, free-flowing material by nitrating 4-acetylamino-anisole and then treating the reaction mixture with water at slightly elevated temperatures, e.g., 20–60° C.

4 Claims, No Drawings

PROCESS FOR PREPARING FREE-FLOWING 2-NITRO-4-ACETYLAMINO-ANISOLE

This is a continuation of application Ser. No. 613,832, filed Sept. 16, 1975, now abandoned.

BACKGROUND

This invention relates to a process for the preparation of 2-nitro-4-acetylamino-anisole directly in the form of a free-flowing moist material.

It is known that 2-nitro-4-acetylamino-anisole can be prepared by dissolving 4-acetylamino-anisole in sulphuric acid, nitrating it with a mixture of nitric acid and concentrated sulphuric acid and pouring the reaction mixture onto ice. The 2-nitro-4-acetylamino-anisole prepared in this way precipitates as a paste of high water content and can only be isolated with great difficulty, for example on a suction filter. Before further processing it must be washed and dried.

SUMMARY

It has been found that 2-nitro-4-acetylamino-anisole is obtained by nitration of 4-acetylamino-anisole as a free-flowing moist material which can be processed further without additional drying, if the reaction mixture obtained after the nitration is treated with water at a slightly elevated temperature.

The free-flowing moist material, as obtained in accordance with the process of the invention, is of granular consistency and can easily be isolated on a suction filter. The reaction product can, without further treatment, be poured and/or packaged and/or employed in a subsequent reaction.

DESCRIPTION

Compared to the state of the art, the reaction product obtained in accordance with the process of the invention contains more 2-nitro-4-acetylamino-anisole and less water than the pasty crude product from conventional processes, and does not have to be dried.

In order to prepare 2-nitro-4-acetylamino-anisole as a free-flowing moist material the nitration is first carried out with a mixture of nitric acid and sulphuric acid in a known manner (German Pat. No. 101,778), and the reaction mixture is then treated, in accordance with the invention, with water at slightly elevated temperature. Preferably, water at a temperature of 20° to 60° C., and particularly preferentially of 30° to 50° C., is used.

In detail, the preparation of 2-nitro-4-acetylamino-anisole as a free-flowing moist material can be carried out as follows in accordance with the process of the invention.

4-Acetylamino-anisole is dissolved in 96% strength by weight sulphuric acid and is then nitrated at −5° to 0° C. with a mixture of nitric acid and sulphuric acid. The reaction mixture is then introduced into water at 30° C., after which the temperature is allowed to rise to 50° C.

The temperature of 50° C. is maintained by metering the reaction mixture and by controlling the cooling. After the entire reaction mixture has been introduced into the water, the batch is cooled to 20° C. and the reaction product which has precipitated is filtered off on a suction filter.

It is surprising that 2-nitro-4-acetylamino-anisole is not hydrolysed in an acid reaction mixture on treatment with water at slightly elevated temperature, since substituted acetanilides decompose in acid solution even at temperatures below 50° C. Thus, 2-(1-butin-3-yloxy)-acetanilide is completely hydrolysed in acid solution even at 35° to 40° C. (Published German Application, 2,063,503). Moreover, it is known that 3-alkyl-5(p-acetaminobenzenesulphonylamino)1,2,4-oxadiazole is hydrolysed to the aniline derivative in acid solution even at 20° C. (Japanese Pat. No. 7,007,739).

Furthermore, it is known that β-(4-acetylamino-phenylsulphonyl)-ethyl sulphate is hydrolysed to the aniline derivative in aqueous sulphuric acid at 30° to 35° C. (Japanese Pat. No. 7,027,096).

The process according to the invention permits the advantageous preparation of 2-nitro-4-acetylamino-anisole as free-flowing moist material having a solids content of 50-70%, which can readily be filtered off and which no longer requires drying before further processing. As a consequence, the isolation of the reaction product can be carried out in a short time and the drying process is made unnecessary.

2-Nitro-4-acetylamino-anisole is, for example, an intermediate product for water-insoluble azo dyestuffs (German Pat. No. 1,220,061).

EXAMPLE 1

610 kg of 4-acetylamino-anisole (98% strength by weight) are dissolved in 2,564 kg for sulphuric acid (96% strength by weight) and are then nitrated with 660 kg of a mixed acid consisting of 33% by weight of nitric acid, 47.5% by weight of sulphuric acid and 19.5% by weight of water, at −3° C. The reaction mixture is then introduced, whilst stirring, into an open vessel containing 5,350 l of water at 30° C. The temperature is allowed to rise to 50° C. and is kept constant by cooling as long as the reaction mixture is being run in. Thereafter the suspension is cooled to 20° C. and stirred for a further hour. The reaction product is filtered off on a suction filter and washed with water until the wash water retains only a weakly acid reaction (pH ~ 4). The filtration and washing process is complete after at most 2 hours.

1,128 kg of a free-flowing reaction product containing 61% of 2-nitro-4-acetylamino-anisole are obtained. This corresponds to a yield of 688.4 kg of dry 2-nitro-4-acetylamino-anisole, which corresponds to 90% of theory.

EXAMPLE 2 (EXAMPLE FOR COMPARISON WITH EXAMPLE 1)

610 kg of 4-acetylamino-anisole (98% strength by weight) are dissolved in 2,564 kg of sulphuric acid (96% strength by weight) and are then nitrated with 660 kg of a mixed acid consisting of 33% by weight of nitric acid, 47.5% by weight of sulphuric acid and 19.5% by weight of water, at −3° C. Thereafter the reaction mixture is added to 5,350 kg of ice water. The mixture is stirred for a further hour at 0° C. and the product is filtered off on a suction filter and washed with water until the wash water retains only a weakly acid reaction (pH ~ 4). The filtration and washing require at least 20 hours.

2,181 kg of a moist paste containing 30% of 2-nitro-4-acetylamino-anisole are obtained. This corresponds to a yield of 654.3 kg of dry 2-nitro-4-acetylamino-anisole, which corresponds to 86% of theory.

In each of Examples 3 to 6, 383.4 g of a reaction mixture which is produced by nitration of 61 g of 4-acetylamino-anisole (98% strength) in 256.4 g of sulphuric acid (96% strength by weight) with 66 g of a mixed acid consisting of 33% by weight of nitric acid, 47.5% by weight of sulphuric acid and 19.5% by weight of water at −3° C., are employed.

EXAMPLE 3

383.4 g of the reaction mixture are added dropwise over the course of 15 minutes to 535 g of water at 30° C. In the course of the addition, the temperature is allowed to rise to 50° C. The remainder of the solution is added, whilst cooling, in such a way that 50° C. is not exceeded. The suspension is stirred for a further hour at 50° C. and then cooled to 20° C. and the precipitate is filtered off and washed with 50 ml of water within 3 minutes.

139.0 g of a free-flowing reaction product containing 45% of 2-nitro-4-acetylamino-anisole are obtained. This corresponds to a yield of 62.6 g of dry 2-nitro-4-acetylamino-anisole, which corresponds to 82.4% of theory.

EXAMPLE 4 (EXAMPLE FOR COMPARISON WITH EXAMPLE 3)

383.4 g of the reaction mixture are added dropwise over the course of 20 minutes to 535 g of ice water. A fine precipitate separates out and is stirred for a further hour at 0° C. The reaction product is then filtered off on a suction filter and washed with 50 ml of water within 3 minutes.

301.3 g of a moist paste containing 21.9% of 2-nitro-4-acetylamino-anisole are obtained. This corresponds to a yield of 66 g of dry 2-nitro-4-acetylamino-anisole, which corresponds to 86.8% of theory.

EXAMPLE 5

383.4 g of the reaction mixture are added dropwise over the course of 10 minutes to water at 30° C. and the mixture is then allowed to warm to 50° C. It is stirred for a further hour at 50° C., after which it is cooled to 30° C. The precipitate is filtered off and washed with 100 ml within 6 minutes.

166.5 g of a reaction product containing 39.4% of 2-nitro-4-acetylamino-anisole are obtained. This corresponds to a yield of 65.6 g of dry 2-nitro-4-acetylamino-anisole, which corresponds to 86.3% of theory.

EXAMPLE 6 (EXAMPLE FOR COMPARISON WITH EXAMPLE 5)

383.4 g of the reaction mixture are added dropwise over the course of 20 minutes to 535.0 g of ice water. A precipitate forms and is stirred for a further hour at 0° C. The product is then filtered off on a suction filter and washed with 100 ml of water within 6 minutes.

409.6 g of a moist paste containing 15.3% of 2-nitro-4-acetylamino-anisole are obtained. This corresponds to a yield of 62.7 g of dry 2-nitro-4-acetylamino-anisole, which corresponds to 82.5% of theory.

What is claimed is:

1. In a process for preparing 2-nitro-4-acetylamino-anisole wherein 4-acetylamino-anisole is nitrated with a mixture of nitric acid and sulfuric acid, the improvement for obtaining the 2-nitro-4-acetylamino-anisole in the form of a free-flowing moist material which comprises contacting the resultant nitration mixture with water at a temperature of 20° to 60° C. by metering the reaction mixture into water and controlling the cooling thereof.

2. A process according to claim 1 wherein the nitration is effected at −5° to 0° C.

3. A process according to claim 1 wherein the nitration mixture is contacted with water at a temperature between 30° and 50° C.

4. A process according to claim 1 wherein following contact of the nitration mixture with water the resultant mixture is thereafter cooled to 20° C.

* * * * *